United States Patent [19]
Wexelman

[11] Patent Number: 5,388,994
[45] Date of Patent: Feb. 14, 1995

[54] VISUAL STIMULATION DEVICES

[76] Inventor: David Wexelman, 531/16 Kiryat Kaminetz, Jerusalem, Israel

[21] Appl. No.: 239,871

[22] Filed: May 10, 1994

[51] Int. Cl.6 .............................................. G09B 19/00
[52] U.S. Cl. ................................................... 434/236
[58] Field of Search ..................... 434/236, 262; 128/6, 128/24.1; 40/442

[56] References Cited

U.S. PATENT DOCUMENTS

| | | | |
|---|---|---|---|
| 3,278,676 | 10/1966 | Becker | 178/6 |
| 3,773,049 | 11/1973 | Rabichev et al. | 128/362 |
| 3,790,772 | 2/1974 | Newman et al. | 240/10 R |
| 4,279,088 | 6/1981 | Hyre | 40/442 |
| 4,483,681 | 11/1984 | Weinblatt | 434/236 |
| 4,553,534 | 11/1985 | Stiegler | 128/24.1 |
| 4,692,118 | 9/1987 | Mould | 434/236 |
| 4,698,564 | 10/1987 | Slavin | 318/257 |
| 4,717,343 | 1/1988 | Densky | 434/262 X |
| 4,728,293 | 3/1988 | Kole, Jr. | 434/236 |
| 4,734,037 | 3/1988 | McClure | 434/236 |
| 4,734,038 | 3/1988 | Dennis | 434/236 |

FOREIGN PATENT DOCUMENTS 8705139  8/1987  WIPO ................................. 434/236

Primary Examiner—William E. Stoll
Attorney, Agent, or Firm—Charles E. Temko

[57] ABSTRACT

The disclosure relates to devices for inducing self hypnosis, as well as for teaching emotionally disturbed children. It utilizes momentary serial reflections of a user from a mirror with interspersed exposure to opaque colored areas, or combination of words, pictures, letters, numbers, etc. The repetity of exposure is variable under control of the user, and above certain cyclic rates, the impression upon the user is totally subliminal, and at the slowest speeds, completely hypnotic.

6 Claims, 5 Drawing Sheets

VISUAL STIMULATION DEVICES

BACKGROUND OF THE INVENTION

This invention relates generally to the field of psychology, educational psychology holistic healing, and religion. More specifically, it relates to devices used for meditation, self-hypnosis, teach and tension alleviation.

Devices for creating visual stimulation of a user are known in the art, as exemplified by U.S. Pat. Nos. 4,279,088; and 3,278,676. More complex devices are exemplified by U.S. Pat. No 3,773,049. The bulk of these devices are electrically or electronically operated and are relatively complex and expensive to manufacture. This limits widespread use among the purchasing public.

SUMMARY OF THE INVENTION

Briefly stated, the invention contemplates the provision of a mechanically operated device which is relatively inexpensive to manufacture and simple to use while yet being capable of producing visual effects which are better suited to obtain such objectives as self-hypnosis, meditation, tension alleviation, and emotional relaxation.

To this end, the disclosed embodiments are substantially entirely mechanical in construction and operation. In a first embodiment, the user seated in front of the device sees himself in a mirror at periodic intervals forming a part of an operational cycle. This cycle is performed manually at a relatively slow pace, to be followed by acceleration of movement of the mirror to a point where the person can no longer see his image in the mirror, but is affected subliminally by his reflection. The user will see a light between two plates, a white plate and a black plate. This light, to which the user is subliminally conscious has a tension-release on the viewer. The speed may be maintained for a brief period of time, lowered or moved through a regulator, after which power is removed, and the device comes to rest. The process can be repeated as often as is desired. Varieties of color stimuli, words and pictures, can be interchanged on the sides of the mirror prism according to the desired effect and purpose.

In a second embodiment, the device includes a rotating plate having a plurality of segments of different colors, and one segment which is a reflective mirror. In front of the rotating plate is a fixed plate having an opening which corresponds to the shape of the segments on the rotating plate, so that when viewed through the opening, only one segment can be seen at a time. In this embodiment, the rotation of the plate is at relatively slower speeds, so that the effect created is hypnotically visual, rather than subliminal, creating the perfect mood for meditation, deep relaxation, or self hypnosis.

BRIEF DESCRIPTION OF THE DRAWINGS

In the drawings, to which reference will be made in the specification, similar reference characters have been employed to designate the corresponding parts throughout the several views.

DETAILED DESCRIPTION OF THE DISCLOSED EMBODIMENTS

Figure 1:
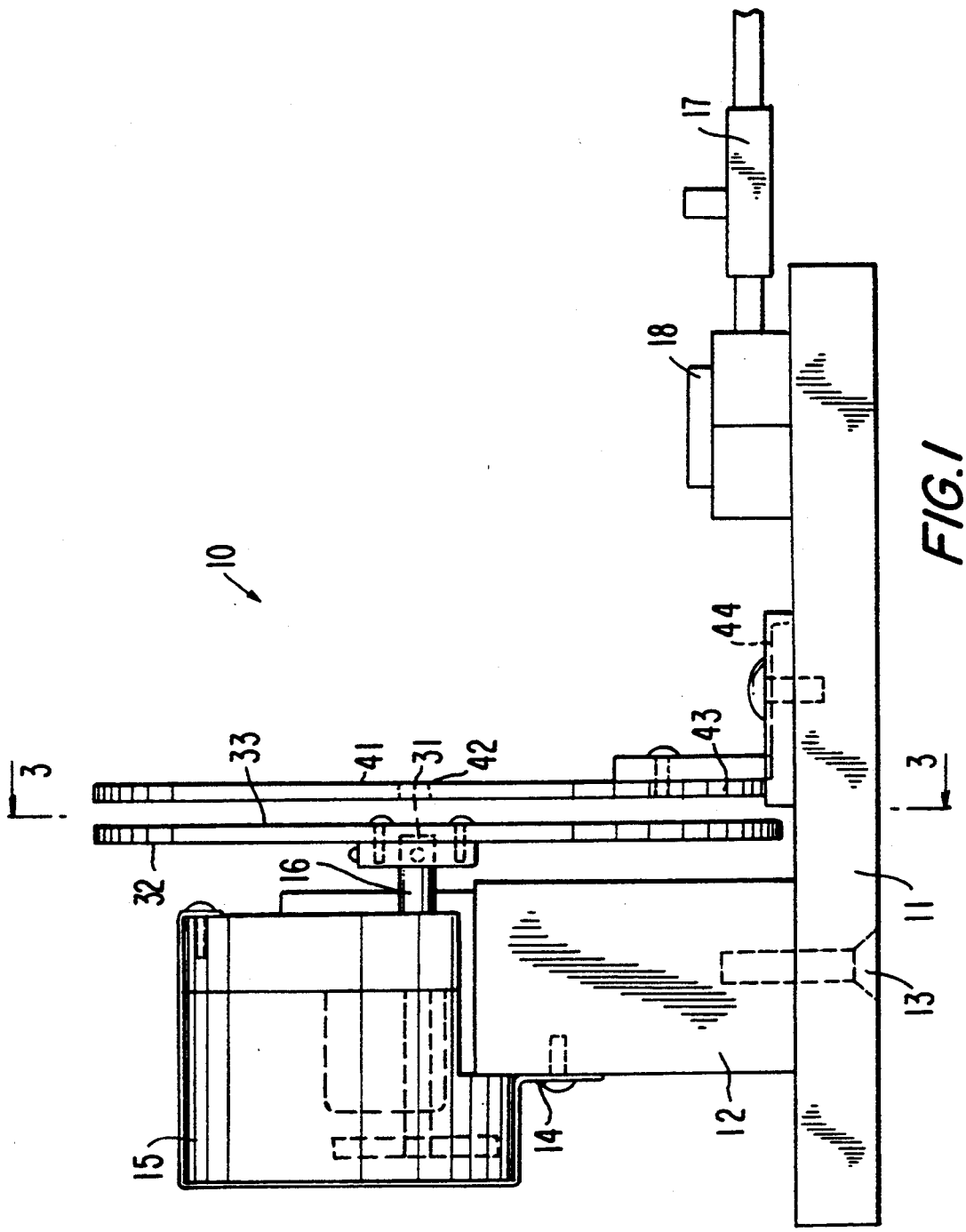
FIG. 1 is a schematic side elevational view showing a first embodiment of the invention.
Figure 2:
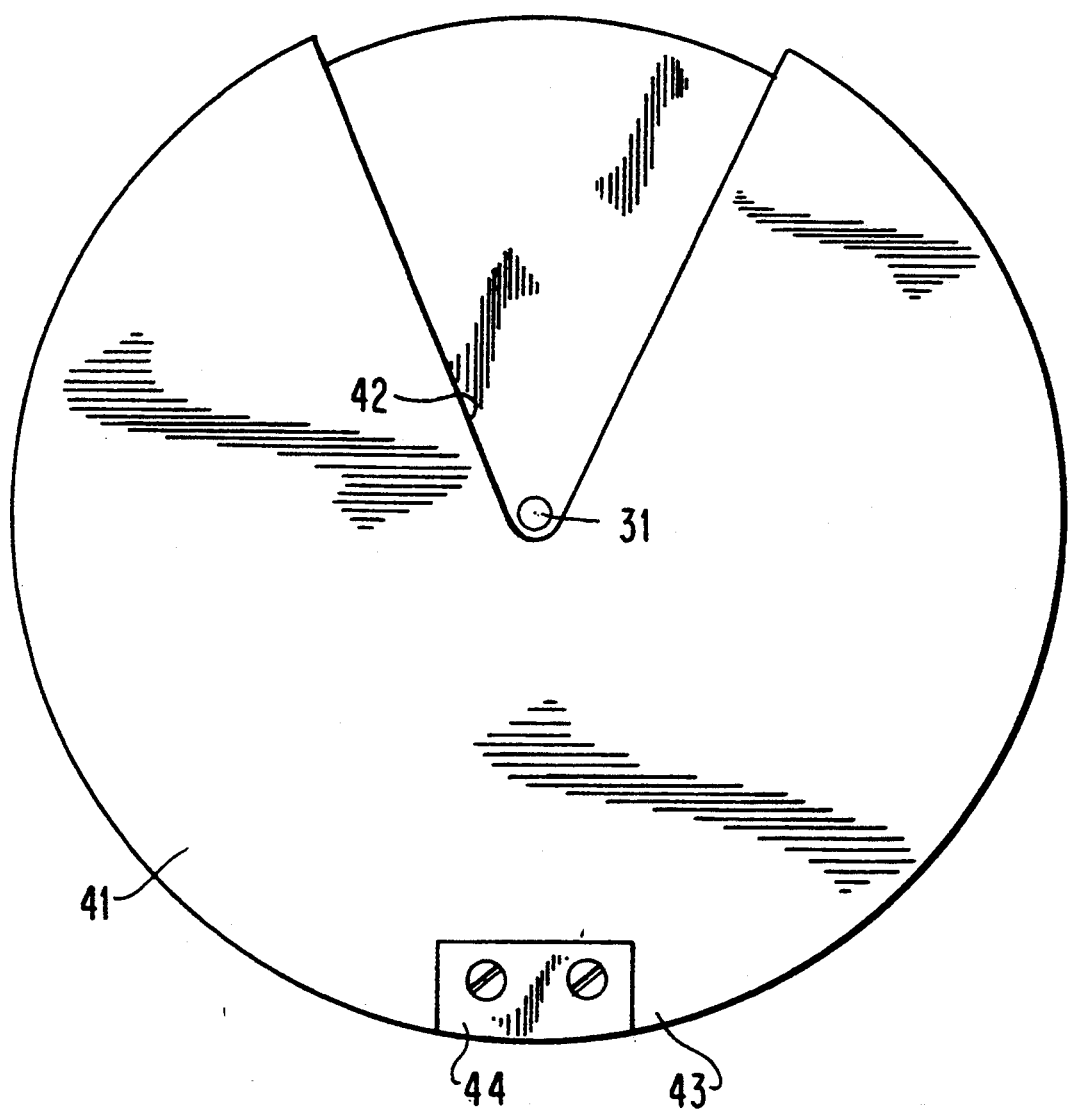
FIG. 2 is a corresponding schematic front elevational view thereof.
Figure 3:
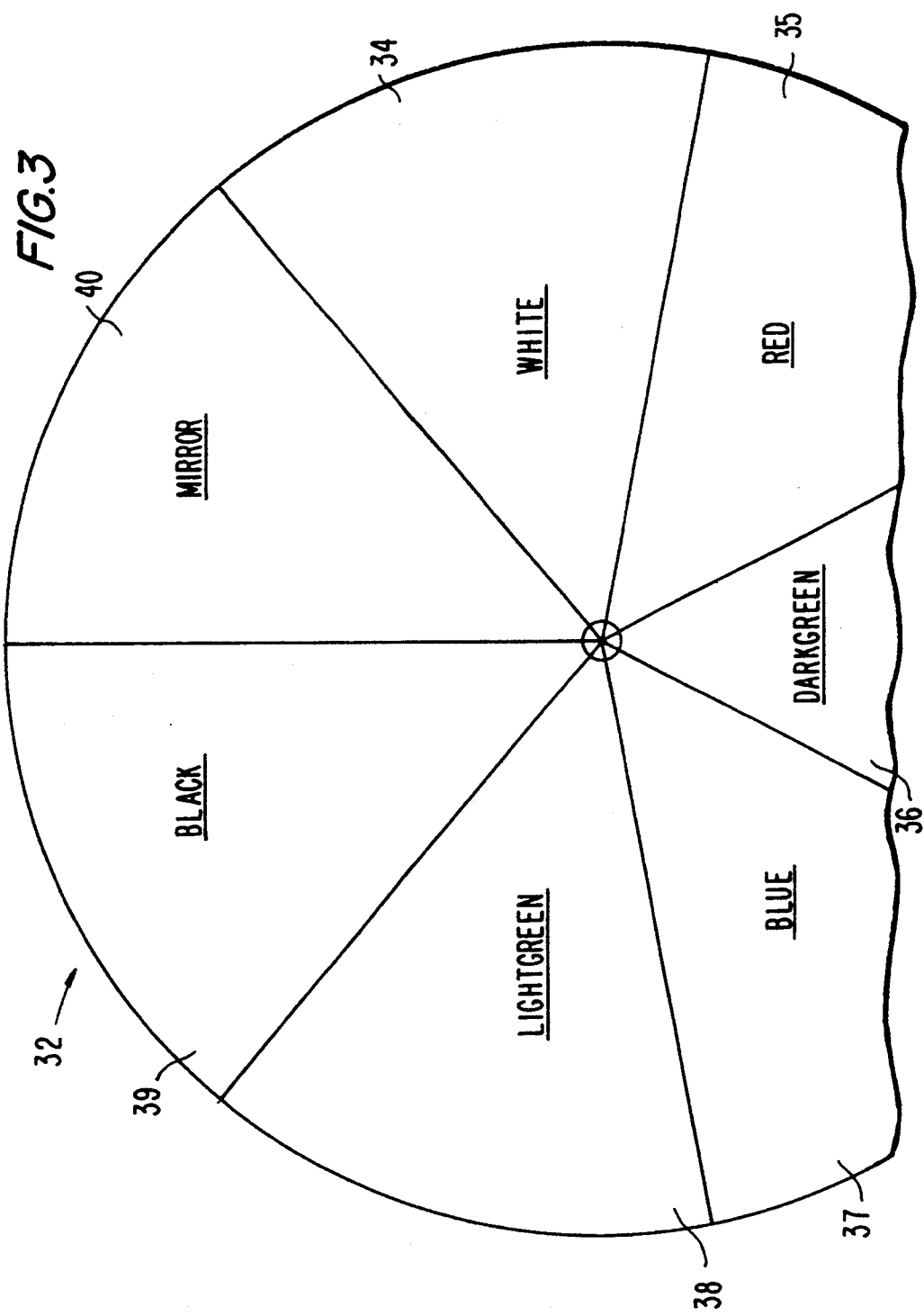
FIG. 3 is a fragmentary sectional view as seen from the plane 3—3 in FIG. 1.

Referring to FIGS. 1-3, inclusive, the first embodiment of the invention, generally indicated by reference character 10, is supported upon a planar base element 11. A spacing block 12 is interconnected thereto by screw means 13 and supports a motor bracket 14 in turn supporting a small electric motor 15, which may be battery operated, but preferably powered by alternating current.

The motor 15 includes an output shaft 16. Speed of rotation is governed by an off-on switch 17, and a rheostat 18. An end segment 31 of the shaft 16 mounts a circular plate element 32 having forward surface 33 divided into seven pie-shaped radially oriented segments 34, 35, 36, 37, 38, 39 and 40. The segments 34-38 are painted or coated in differing colors, while the segment 40 forms a mirror surface.

Positioned in front of the plate element 32 is a planar mask element 41 having an opening 42 through which the end segment 31 projects. A lower end 43 thereof is supported by a bracket 44 on the plate 11.

In use, the device is initially operated at a slow rotative speed. In the disclosed embodiment, the six colors employed are black, white, red, blue, green, and light green. These are exposed to view through the mask element for serial viewing for the creating of differing visual and thought stimulation. Other colors may be substituted, and words or other symbols (not shown) may also be placed upon the surfaces to enable the user to place these words in memory with repeated exposure. The seventh interval enables the viewer to briefly see his reflection to enable self revelation, or to meditate on a particular thought stimulus substituted for the mirror. After a brief period, the speed of rotation is increased for a period of time where the impressions received by the viewer are more frequent (twenty times per minute), following which the rotation should be again slowed to reach a very slow hypnotic speed where the user can close his eyes and automatically enter meditation on the visual stimulus and thoughts on the disk.

The effect upon the user of the colors and the mirror reflection create a peaceful, tranquil and hypnotic atmosphere. Where a psychologist assists the user operating the machine, it is possible to enhance the process through talking with the user, with instructions prepared by the psychologist according to the user's needs. As the speed of the machine is slowed, the user at the same time slows his own mind activity, thus imparting to the user a feeling of peace and tranquility, and the ability to enter into deep relaxation by closing his eyes.

Where the segments are provided with symbols, or suggestive words, a though process can be implanted in the mind of the user which will enable desired behavior in the individual after treatment has ceased. For example, the segments may be provided with the words "I want to stop smoking", each word being exposed during a different interval.

Figure 4:
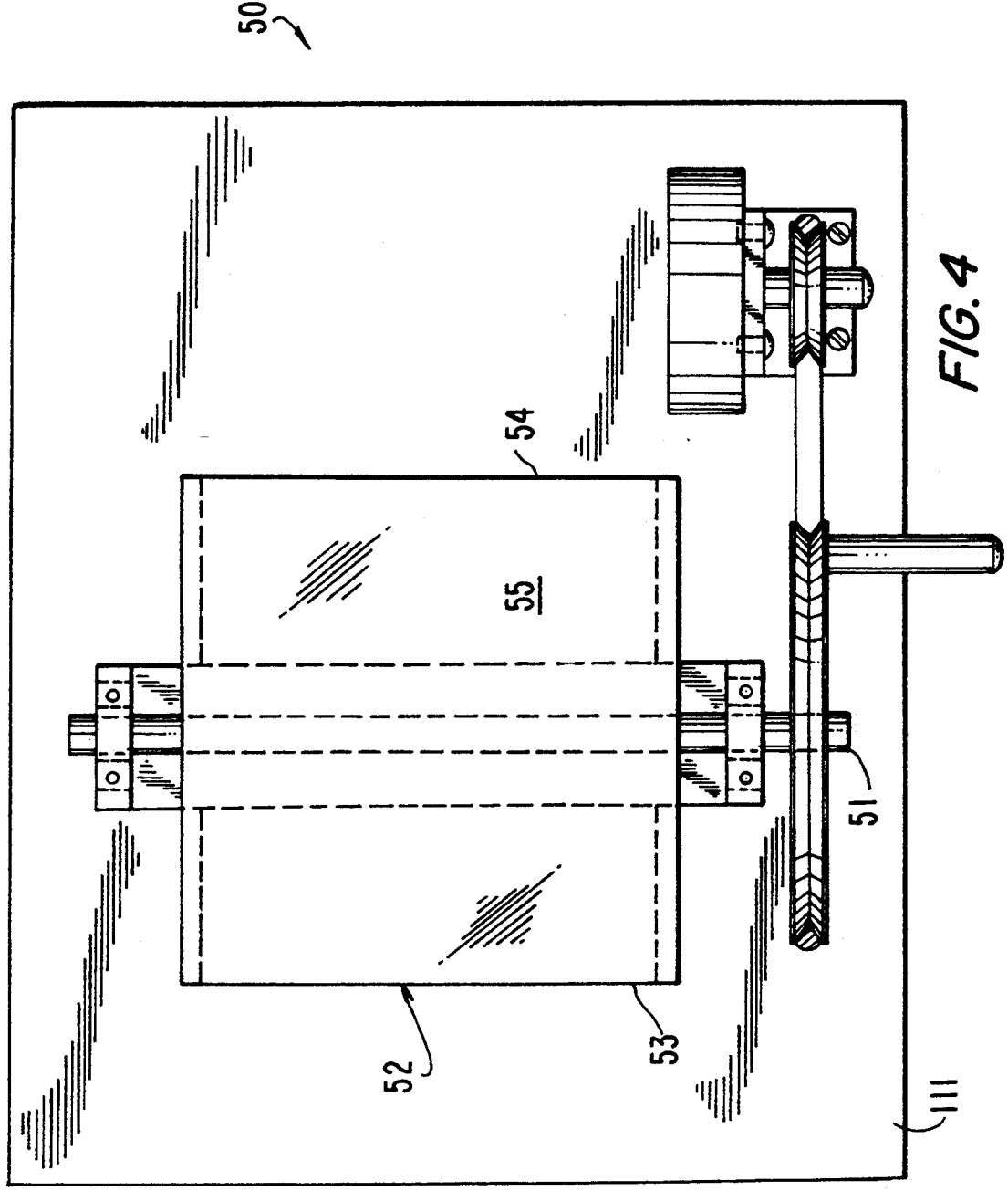
FIG. 4 is a top plan view of a second embodiment of the invention.
Figure 5:
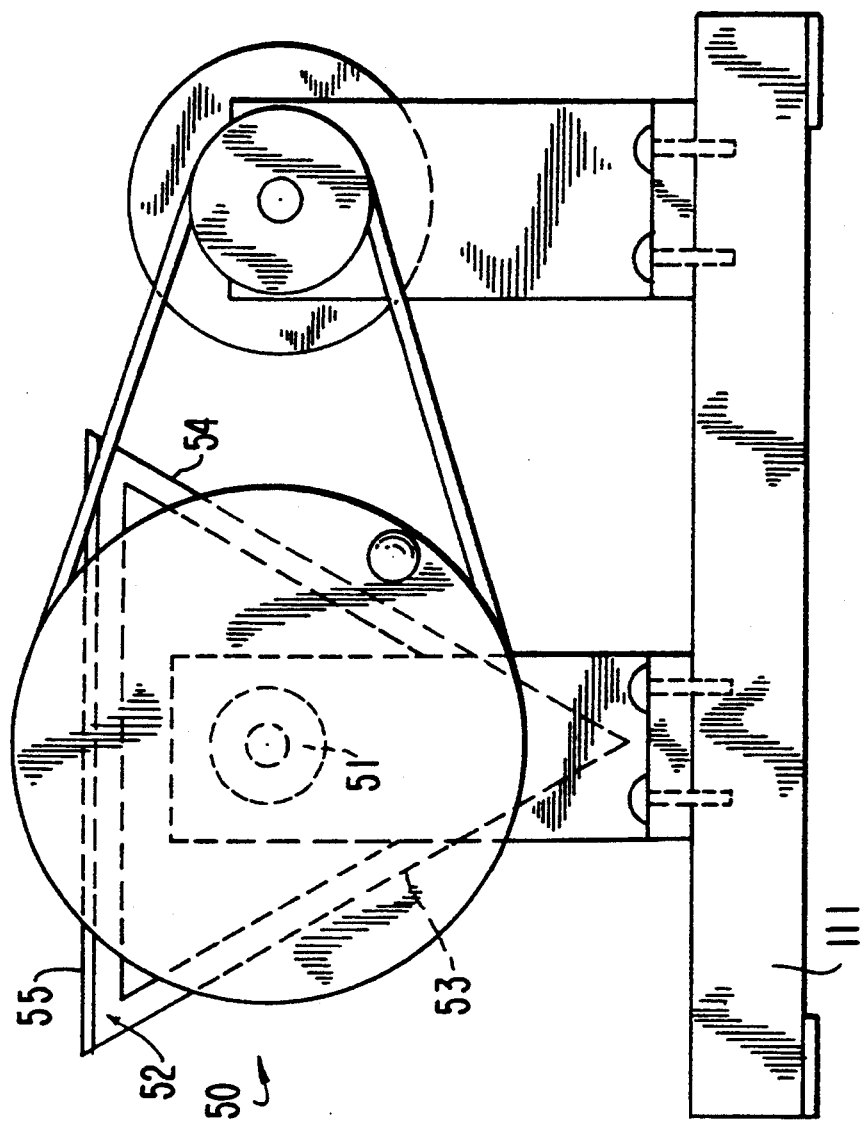
FIG. 5 is a side elevational view of the second embodiment.

Turning now to the second embodiment of the invention generally indicated by reference character 50, (FIGS. 4 and 5) parts corresponding to those of the principal embodiment have been designated by similar reference characters with the additional prefix "1".

In the second embodiment, construction is somewhat simplified, and a driven shaft 51 mounts a triangular prism 52 having three exposed surfaces which are serially presented to the viewer. These include a white colored surface 53, a black colored surface 54, and a reflective mirror surface 55. Because only one surface is exposed to view at any given instant, no masking element is required, and the mirror surface, being one of only three surfaces, is exposed at faster cyclic frequency, enabling the user to think about himself in greater depth. It is possible to use the first and second embodiments in conjunction with each other, through which the meditative and hypnotic effect is received by the user without requiring him to close his eyes except for an instant. The secret of this phenominum is that the mind itself in meditation or deep thought operates on two levels of thought. One is the subliminal level of thought frequency, and the slowing of thought frequency.

I wish it to be understood that I do not consider the invention to be limited to the precise details of structure shown and set forth in the specification, for obvious modifications will occur to those skilled in the art to which the invention pertains.

I claim:

1. A visual stimulative device comprising: a rotating element having an axis of rotation and having plural planar surfaces thereon, each of said surfaces being in identical fixed relation relative to said axis of rotation, one of said planar surfaces having a reflective mirror, the remainder of said surfaces being of different colors; and means for powering said rotating element at varying angular velocity whereby a viewer is serially exposed to each of said planar surfaces in repetitive cycles.

2. A device in accordance with claim 1, in which said rotating element is of prismatic configuration.

3. A device in accordance with claim 1 in which said rotating element is an arcuate planar plate having plural radial segments thereon of different colors, with one of said segments being a reflective mirror.

4. A visual simulation device comprising: a rotating plate element having an exposed surface, said surface being divided into plural radially oriented segments, a first of said segments having a reflective surface thereon, the remaining surfaces being substantially non-reflective, and of differing colors; masking means positioned to overlie said exposed surfaces and having an aperture through which only one of said segments may be viewed at any given instant; and means for rotating said plate relative to said masking means whereby a viewer observes each of said segments in serial manner as said segments pass said aperture.

5. A device in accordance with claim 4, including electrically powered motor means for rotating said plate.

6. A device in accordance with claim 5, including means for varying the speed of said plate relative to said masking means.

* * * * *